United States Patent [19]

Jinotti

[11] Patent Number: 5,496,287
[45] Date of Patent: Mar. 5, 1996

[54] PULMONARY SUCTION CATHETER

[76] Inventor: Walter J. Jinotti, 10 Scott St., New Brunswick, N.J. 08903

[21] Appl. No.: 270,768

[22] Filed: Jul. 5, 1994

[51] Int. Cl.⁶ ........................................ A61M 5/00
[52] U.S. Cl. .................. 604/249; 604/31; 604/33; 604/254; 251/337
[58] Field of Search ................. 604/31, 33, 246, 604/249, 256; 251/149.3, 149.6, 321–323, 337; 137/625.48

[56] References Cited

U.S. PATENT DOCUMENTS

| | | | |
|---|---|---|---|
| 2,669,233 | 2/1954 | Friend | 604/33 |
| 4,423,741 | 1/1984 | Levy | 604/249 |
| 4,757,919 | 7/1988 | Smazik et al. | 251/149.6 |
| 4,759,527 | 7/1988 | Brown et al. | 251/321 |
| 5,147,333 | 9/1992 | Raines | 604/256 |
| 5,364,070 | 11/1994 | Crow | 251/323 |

*Primary Examiner*—C. Fred Rosenbaum
*Assistant Examiner*—Laird J. Knights
*Attorney, Agent, or Firm*—Robert A. Green

[57] ABSTRACT

The disclosure is of a suction catheter having a valve body including a vertical plunger in a vertical bore and two horizontal tubes, one for connection to a source of suction and one for connection to a patient. In one position of the plunger, the two tubes are aligned with a path through the plunger to provide suction to the patient. In another position of the plunger, the tube connected to the suction is led to the atmosphere whereby suction is completely removed from the patient.

4 Claims, 1 Drawing Sheet

PULMONARY SUCTION CATHETER

BACKGROUND OF THE INVENTION

One type of pulmonary suction catheter is known for applying suction to the lungs of a patient. This catheter is inserted into a patient's lungs and the operator manipulates the catheter to permit suction to be applied from a wall source in a room to remove mucus from the lungs. The wall source is always on. When the operator wishes to discontinue the flow of suction from the patient, the catheter must be removed from the patient because with the wall source still suctioning through the catheter apparatus and, by a Venturi effect, the suction source draws air through the catheter and it also draws air and oxygen from the patient. Clearly, this is an undesirable happening for the patient.

There is no suctioning device presently available which can perform suction when desired but in which the suction can be removed from the patient without removing the catheter from the patient and without turning off the wall supply.

SUMMARY OF THE INVENTION

The invention includes a valve comprising a solid body having a vertical through-hole or bore and horizontally aligned tubes disposed on each side of said vertical through hole, one being couplable to a patient and the other being couplable to a suction source. A plunger is slidably mounted in the vertical through-hole and includes a portion which is adapted to be in alignment with the horizontally aligned tubes to apply suction to a patient. One of the horizontal tubes includes means for coupling to a catheter to be inserted in a patient and the other horizontal tube includes means for coupling to a source of suction.

An auxiliary hole is provided in the housing which couples the outside atmosphere through the horizontal hole to the suction source to permit the patient to be disconnected from the suction source.

The device of the invention, can be operated to apply suction and it can be held in the patient's lungs without the above-described Venturi effect taking place and without oxygen depletion taking place in the patient.

DESCRIPTION OF THE INVENTION

Figure 3:
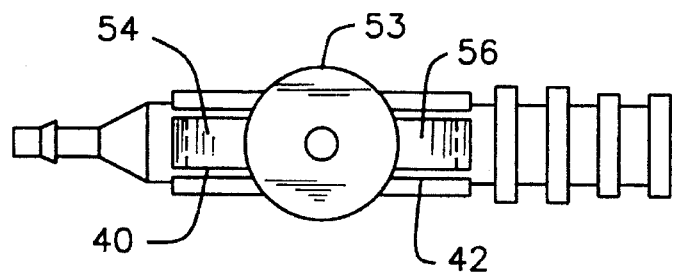
FIG. 3 is a plan view of the apparatus of FIG. 1.

A pulmonary suction catheter assembly 10 embodying the invention includes a valve device 14 which includes a solid rigid body 10 of a suitable plastic, such as polyvinyl chloride. The body has a vertical through-hole or bore 30. A pair of aligned left and right horizontal tubes 40 and 42, respectively, are aligned with each other generally along the horizontal axis of the body and extend therefrom the central bore with which they communicate. The left tube is secured to a flexible catheter tube 44 which has a remote end adapted to be inserted into a patient. The right tube 42 is coupled by a suitable flexible tube to a source of suction 48, for example in the wall 50 of a hospital room.

A plunger 50 is slidably mounted in the central vertical bore 30 and comprises a body of a relatively flexible material like rubber or nylon which is sufficiently oversized so that it forms a tight fit in the central bore and thus prevents leakage in use of the apparatus. The plunger carries at its upper end a cap 53 which serves as a push button for ease of operation by a user of the apparatus. A pair of leaf springs 54 and 56 are secured to the cap and they bear against tubes 40 and 42 to urge the plunger upwardly in its normal unactivated state. Other arrangements might be provided to perform this function.

Figure 4:
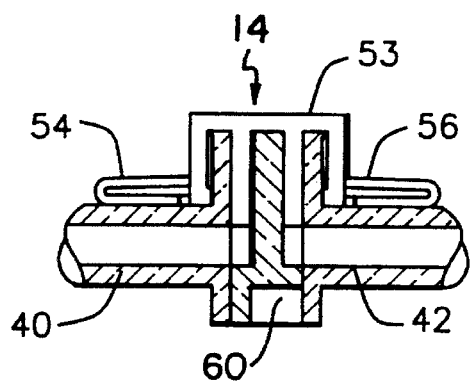
FIG. 4 is a side elevational view of the apparatus in FIG. 1 illustrating its operation.
Figure 2:
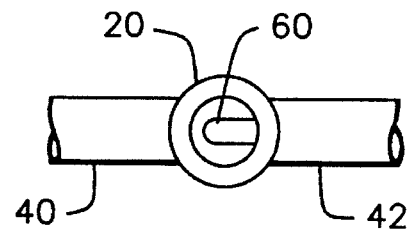
FIG. 2 is a bottom view of the apparatus in FIG. 1.

Below the top button 53 the body of the plunger is redued in diameter to provide a small diameter rib 58 which is positioned so that when the plunger 52 is depressed (FIG. 4), this rib area is aligned with the two horizontal tubes 40 and 42 and provides a continuous open path from the source of suction 48 in the wall 50 through the tubes 40 and 42 and the plunger 52 and to the patient who thus receives suction.

Figure 1:
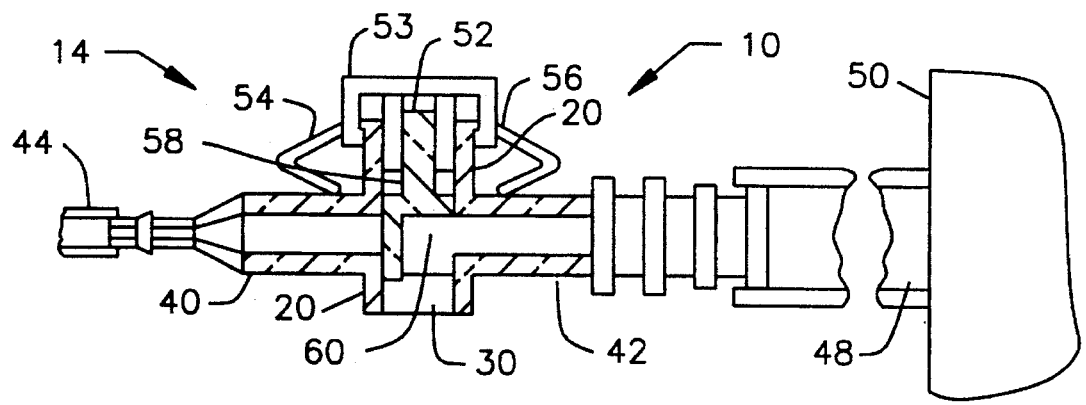
FIG. 1 is a side sectional elevational view of apparatus embodying the invention.

The plunger also includes an opening 60 which is at the bottom of the plunger and includes a horizontal portion 62 which provides an opening in the side wall of the plunger. The opening 60 is positioned in the plunger so that when the plunger is in its upward position (FIG. 1)to remove suction from the patient, the opening 60 is aligned with the horizontal tube 42 and thereby the outside atmoshere is connected to the source of suction. Thus, there is no danger of unwanted suction being applied to the patient.

Thus, to summarize the operation of the assembly 10, when it is desired to apply suction to a patient into whom the tube 44 has been inserted, the operator depresses cap 53 and the tubes 40 and 42 are aligned through the rib 58 and suction flows from the wall source 48 to the patient. When suctioning is completed, the operator pressure on the cap 53 is released, the leaf springs 54 and 56 push the plunger upwardly to the position shown in FIG. 1 and the opening 60 is aligned with tube 42 and the atmosphere is coupled from the bottom of the plunger through tube 42 to the source of suction.

What is claimed is:

1. Apparatus for use in treating a pulmonary patient comprising a valve having a valve body, a first horizontal path through said valve body having a first end and a second end, said first end having means foe coupling to a patient and said second end having means for coupling to a source of suction, a source of suction coupled to said second end of said first horizontal path, a second vertical path through said valve body having an upper end and a lower end, a solid slidable plunger in said vertical path in said valve body, said plunger having an upper end and a lower end and a through hole between its upper and its lower end which can be aligned with said horizontal path through said valve body in one position thereof and can be moved out of alignment with said valve body in a second position thereof, and in sais second position, the solid lower end of said plunger blocking said first end of said first horizontal path through said valve body which goes to a patient, the solid lower end of said plunger having an auxiliary opening which is aligned with and communicates with said second end of said first horizontal path through said valve body and with said source of suction connected thereto when said plunger is in said second position whereby said source of suction communicates with said auxiliary opening in said lower end of said plunger and with the atmosphere with which it communicates, and means coupled to said plunger for sliding it up and down, said means being positioned in and blocking said upper end of said vertical path through said valve body.

2. The apparatus defined in claim 1 wherein said plunger is made of relatively flexible material and forms a tight fit in said vertical bore to prevent leakage therefrom.

3. The apparatus defined in claim 1 wherein said plunger includes a cap and said spring means comprises first and second leaf springs which are secured at one end to said cap and the other ends thereof contact said horizontal tubes.

4. Apparatus for use in treating a pulmonary patient comprising a valve having a hollow tubular valve body, a first generally horizontal patient tube secured to said valve body and communicating with the interior thereof, said patient tube adapted to be coupled to a patient to apply suction thereto, a second suction supply tube secured to said valve body and communicating with the interior thereof, said suction supply tube being generally axially aligned with said patient tube so that a suction path is provided from said suction supply tube, through said valve body into said patient tube, a source of suction coupled to said suction supply tube, said valve body having an open upper end and an open lower end, a slidable plunger in said valve body, said plunger being slidable from a first upper position to a second lower position, a wall portion extending from said lower end of said plunger, said wall portion being aligned with and blocking said patient tube when said plunger is in its first upper position and at the same time there is an air flow path from the open lower end of said valve body along the lower end of said plunger and into said suction tube, a generally horizontal passageway through said plunger positioned between its upper end and its lower end and positioned so that when said plunger is in its second lower position, said passageway is aligned with said patient tube and said suction tube and suction can be administered to a patient, and a spring-biased push button at the upper end of said plunger.

* * * * *